(12) United States Patent
Martin et al.

(10) Patent No.: US 8,343,104 B2
(45) Date of Patent: Jan. 1, 2013

(54) CLOSABLE AND OPENABLE CATHETER ASSEMBLY AND METHOD OF USING SAME

(75) Inventors: John Martin, Annapolis, MD (US); Timothy Schweikert, Levittown, PA (US); Christopher Linden, Allentown, PA (US); Kevin Sanford, Chalfont, PA (US); Mark S. Fisher, Sellersville, PA (US); W. Shaun Wall, North Wales, PA (US); Angela Wentling, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 1220 days.

(21) Appl. No.: 12/164,287

(22) Filed: Jun. 30, 2008

(65) Prior Publication Data
US 2009/0005741 A1    Jan. 1, 2009

Related U.S. Application Data

(60) Provisional application No. 60/937,847, filed on Jun. 29, 2007.

(51) Int. Cl.
*A61M 5/178* (2006.01)
*A61M 1/00* (2006.01)
*A61M 3/00* (2006.01)
*A61M 5/00* (2006.01)
*A61M 5/14* (2006.01)

(52) U.S. Cl. ......... 604/164.02; 604/27; 604/30; 604/33; 604/43; 604/164.01; 604/164.07; 604/164.12; 604/167.01; 604/167.03; 604/246; 604/249; 604/256

(58) Field of Classification Search ............... 604/158, 604/159, 164.01, 164.02, 164.12, 167.01, 604/167.03, 27, 30, 33, 43, 161, 164.07, 604/165.01, 165.02, 246, 249, 256
See application file for complete search history.

(56) References Cited

U.S. PATENT DOCUMENTS
4,170,993 A    10/1979   Alvarez
(Continued)

FOREIGN PATENT DOCUMENTS
WO    WO99/44666    10/1999

*Primary Examiner* — Kevin C Sirmons
*Assistant Examiner* — Shefali Patel
(74) *Attorney, Agent, or Firm* — Glenn M. Massina, Esq.; Fox Rothschild LLP

(57) ABSTRACT

A catheter assembly (10) having an outer catheter (12) and an inner catheter (14) extending coaxially through the outer catheter, and a hub (16). The inner catheter (14) is axially movable within and with respect to the outer catheter (14) by use of an actuator assembly (130) such that the catheter assembly has an opened condition permitting fluid communication with vasculature of a patient, and a closed condition preventing fluid communication with the vasculature of the patient. The opened condition permits the intended use of the catheter assembly such as for hemodialysis of the patient. In the closed condition, locking solution may be maintained in the catheter assembly and later removed therefrom, with essentially no locking solution leaving the catheter assembly or entering the patient. The actuator assembly (130) is secured to a proximal end portion (128) of the inner catheter (14) as it protrudes proximally from the hub (16), where it is accessible to the practitioner. The actuator assembly (130) may comprise an adapter sleeve (90) fixed to the inner catheter (14), and a swivel sleeve (92) which is rotatable with respect to both the adapter sleeve (90) and the hub (16).

29 Claims, 8 Drawing Sheets

U.S. PATENT DOCUMENTS

| | | | |
|---|---|---|---|
| 4,202,332 A | 5/1980 | Tersteegen et al. | |
| 4,917,679 A | 4/1990 | Kronner | |
| 5,318,547 A | 6/1994 | Altschuler | |
| 5,342,379 A | 8/1994 | Volinsky | |
| 5,431,671 A | 7/1995 | Nallakrishnan | |
| 5,472,430 A | 12/1995 | Vaillancourt et al. | |
| 5,591,138 A | 1/1997 | Vaillancourt | |
| 5,688,249 A | 11/1997 | Chang et al. | |
| 5,984,899 A | 11/1999 | D'Alessio et al. | |
| 6,270,489 B1 * | 8/2001 | Wise et al. | 604/508 |
| 6,520,939 B2 * | 2/2003 | Lafontaine | 604/167.03 |
| 6,626,861 B1 | 9/2003 | Hart et al. | |
| 6,723,084 B1 * | 4/2004 | Maginot et al. | 604/535 |
| 6,758,836 B2 | 7/2004 | Zawacki | |
| 6,808,510 B1 | 10/2004 | DiFiore | |
| 6,994,689 B1 | 2/2006 | Zadno-Azizi et al. | |
| 2002/0087108 A1 | 7/2002 | Maginot et al. | |
| 2006/0253063 A1 | 11/2006 | Schweikert | |
| 2008/0009784 A1 * | 1/2008 | Leedle et al. | 604/43 |

* cited by examiner

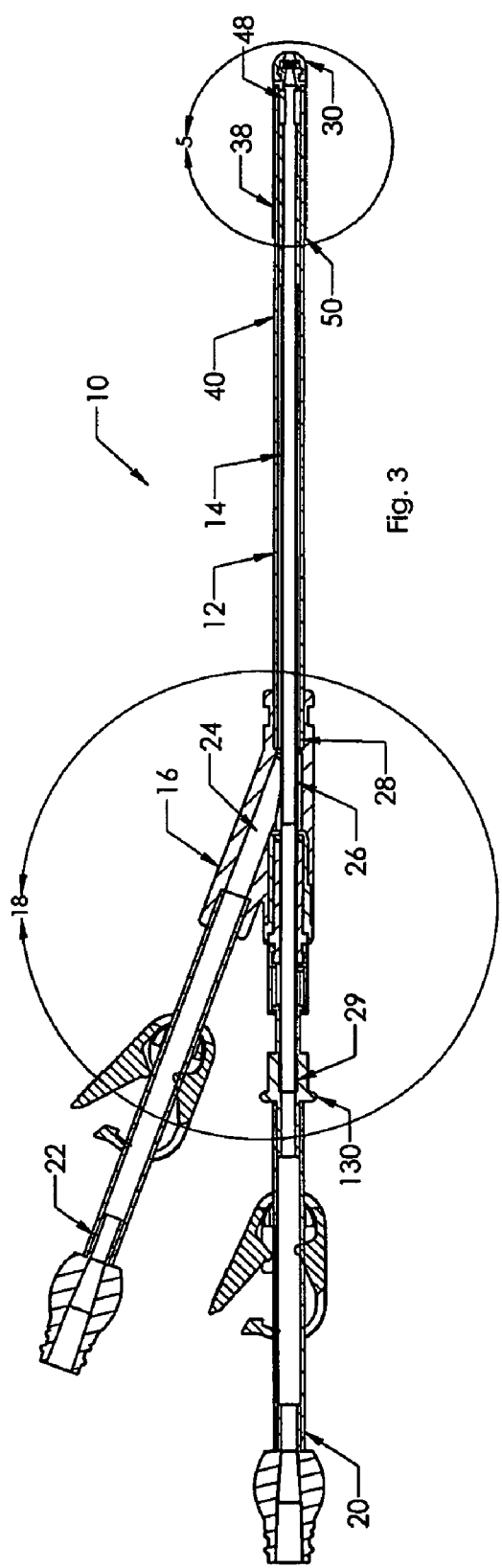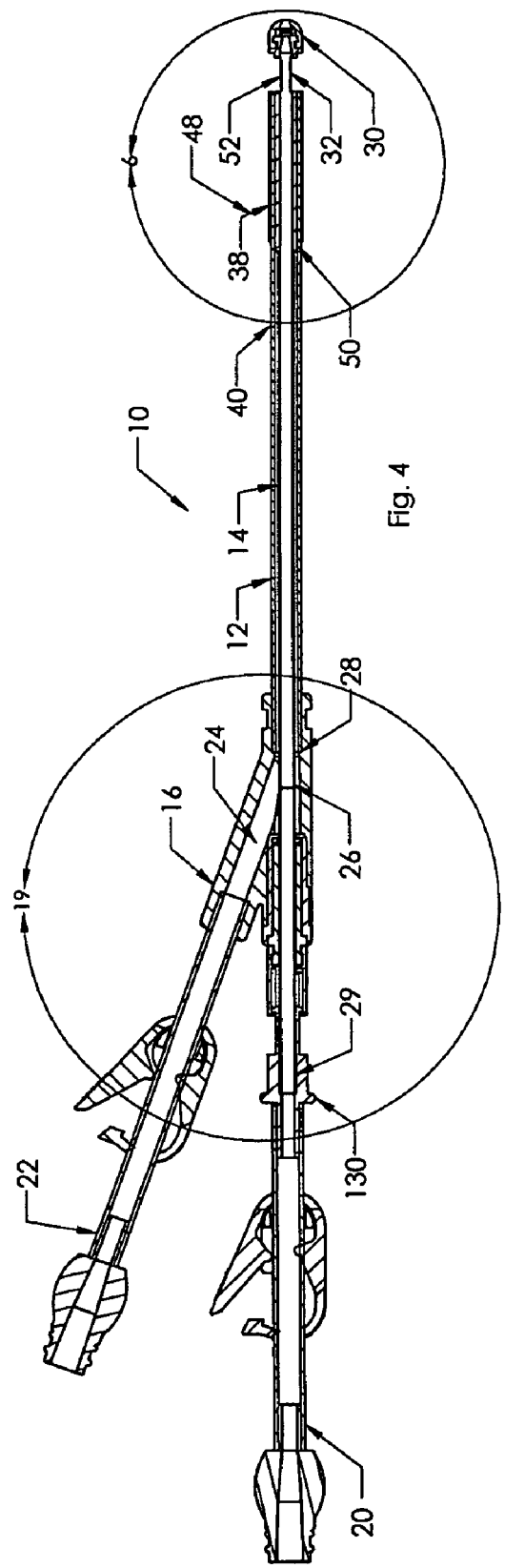

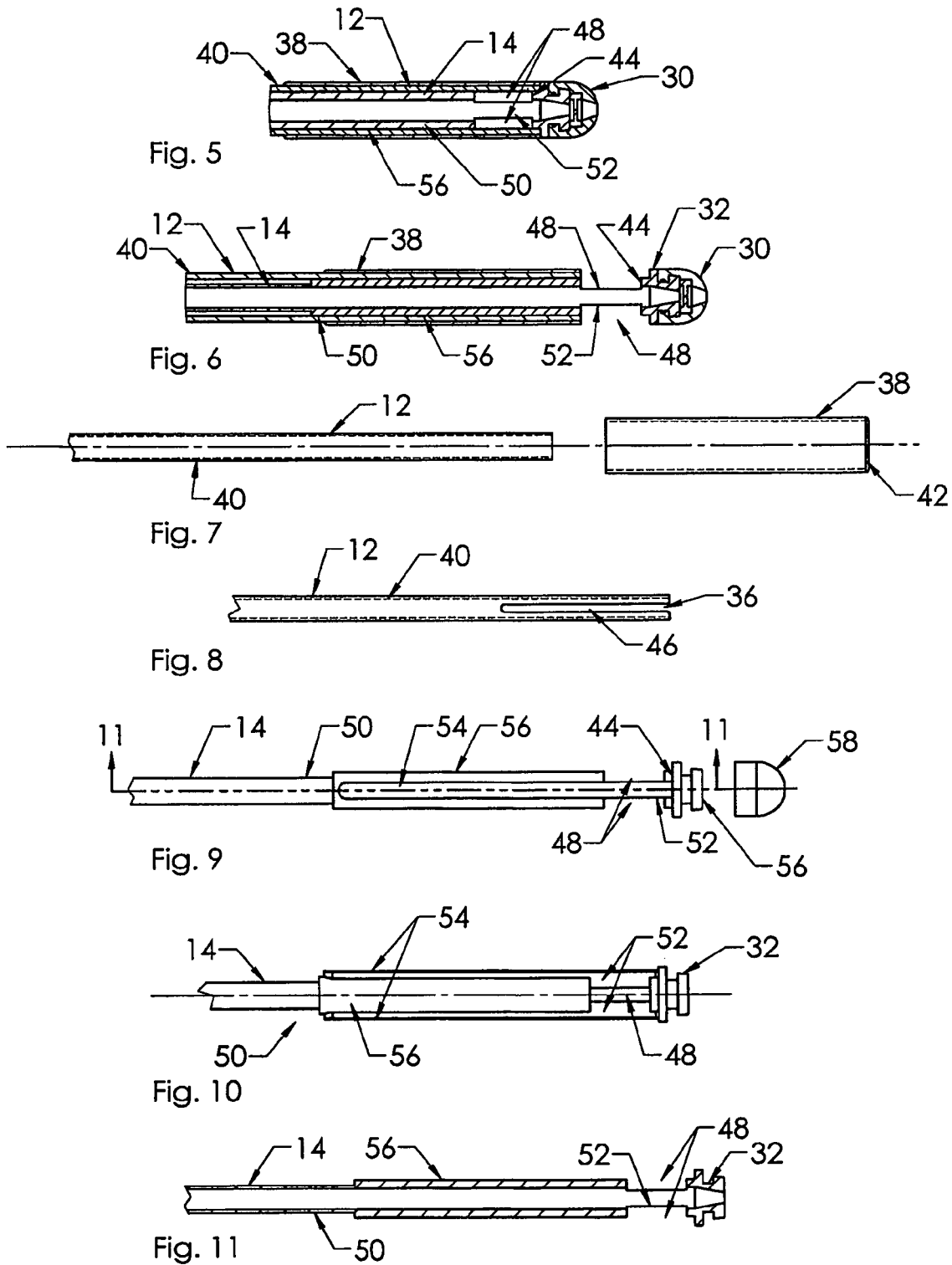

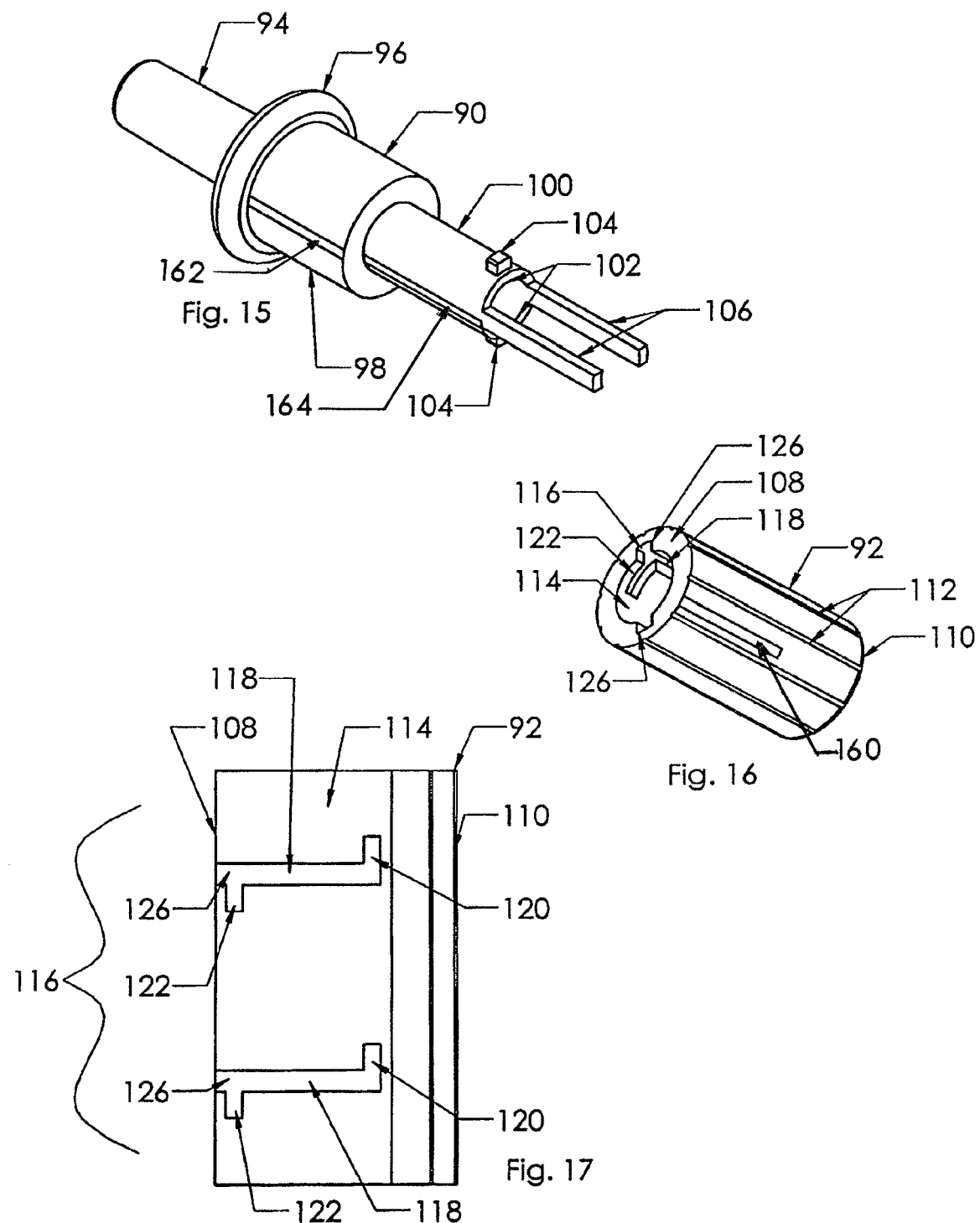

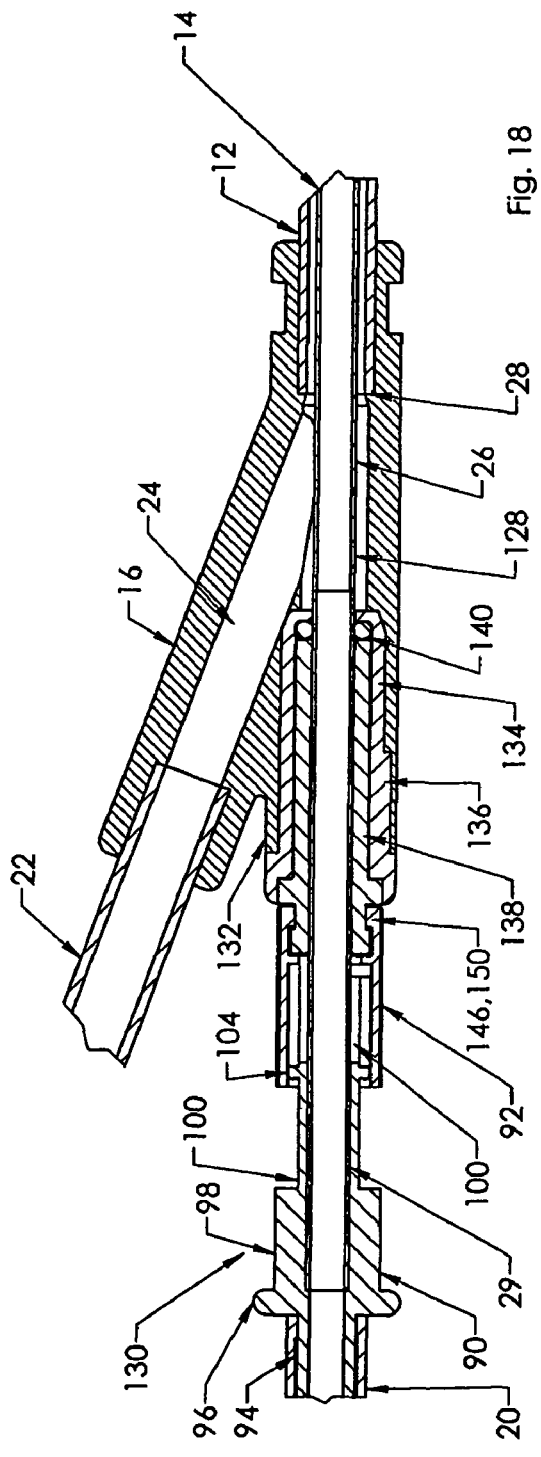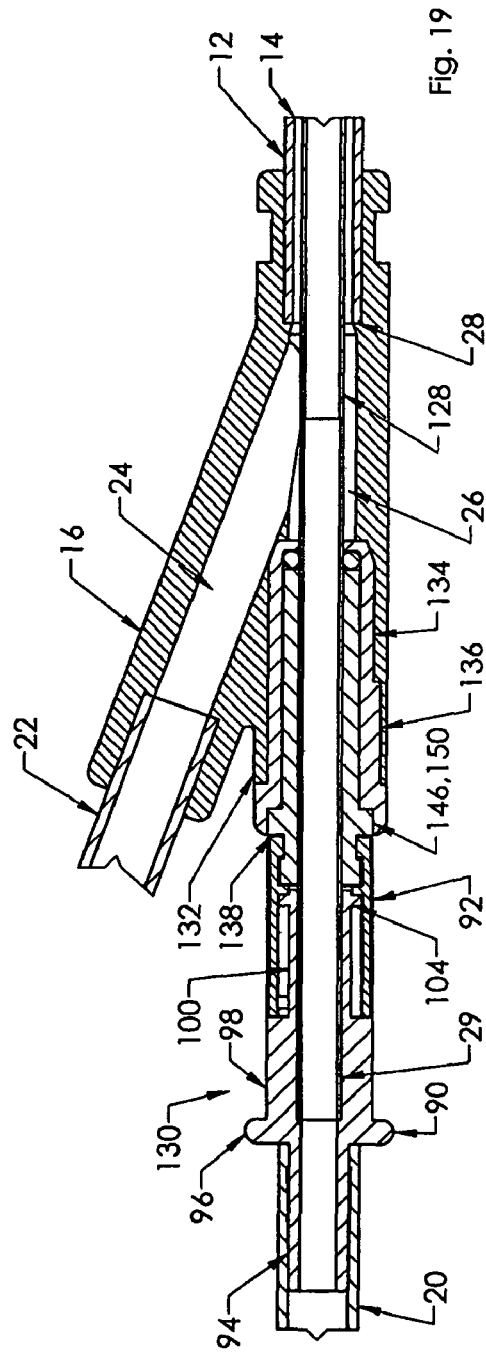

CLOSABLE AND OPENABLE CATHETER ASSEMBLY AND METHOD OF USING SAME

CROSS-REFERENCE TO RELATED APPLICATIONS

This application claims the benefit of U.S. Provisional Patent Application Ser. No. 60/937,847 filed Jun. 29, 2007.

FIELD OF THE INVENTION

This relates to the field of medical devices and more particularly to catheters and catheter assemblies.

BACKGROUND OF THE INVENTION

Hemodialysis catheters are implanted into the vasculature of a patient, and have proximal ends that extend from the patient and are connectable to and disconnectable from tubing of a hemodialysis apparatus. Such catheters are provided with a first lumen and a second lumen coextending to respective distal tips that are carefully positioned at a selected site in a particular vessel of the patient, so that undialysed blood may be withdrawn from the patient's vessel while dialysed blood may be reintroduced into the patient's vessel simultaneously, at respective distal tip openings of the lumens. The catheter lumens may be coextending separate catheters or may be dual (or more than two) lumens of a single catheter separated by a septum wall. The distal tips of the two lumens are generally staggered along the vessel such that blood being withdrawn does not include any significant amount of dialyzed blood that has been reintroduced into the vessel at the more distal of the two distal tips.

When a particular dialysis procedure has been completed, the proximal ends of the catheter are disconnected from the tubes of the hemodialysis apparatus, and the lumens are generally inactive until the subsequent dialysis procedure, although fluid medication or saline may be infused into at least one of the lumens, if and when desired, or a blood sample withdrawn. However, blood is highly susceptible to coagulation and clot formation. The addition of a specific agent or locking solution to the catheter or any extracorporeal blood-contacting surface can reduce the incidence of coagulation by interfering and/or inhibiting the hematological chemistry of blood and its interaction with synthetic materials, such as those from which catheters are made.

It is conventional, then, to introduce anticoagulant locking solutions such as heparin into an implanted catheter between hemodialysis treatments, to prevent clotting of blood within the catheter, and which then is withdrawn for the subsequent dialysis procedure. Between hemodialysis treatments, the catheter is clamped off outside of the patient, creating a pressure gradient that holds the locking solution within the lumens. However, certain amounts of locking solution are known to enter the patient's blood stream through the open distal tips, especially in areas where side holes are present. The amounts introduced into the patient are generally not at a level to cause toxicity or disrupt a patient's hematology; however, the leaching of small amounts of locking solution from the distal lumen tips makes the catheter more prone to lumen clot-off.

One catheter assembly directed to minimizing amounts of locking solution entering the patient's blood stream is disclosed in U.S. Patent Publication No. US 2006/0253063 A1. In this application, the catheter includes a first lumen having a first distal tip, and a second lumen having a second distal tip, wherein the first and second distal tips having wall sections that are normally disposed in a closed position but are each openable under fluid pressure. While both lumens have openable distal tip wall sections, the first distal tip has a flap openable both inwardly and outwardly when the first lumen is subjected to negative pressure and positive pressure, respectively, relative to the blood pressure of the patient in whom the catheter has been implanted. The second lumen extends a selected distance distally of the first distal tip to a second distal tip that is a generally rounded tip when closed, and the second distal tip is defined by an openable section that is internally concave and may be formed by at least one slit cut into a closed rounded distal tip after extrusion of the lumen, defining at least two generally curved lip portions.

With respect to the above-discussed catheter system of Publication No. US 2006/0253063 A1, the several lip portions are openable outwardly under positive pressure applied to the distal end of the second lumen, and a closable together under negative pressure applied to the second lumen. Near the second distal tip, in the side wall of the second lumen are side port sections that are openable inwardly upon application of negative pressure to the proximal end of the second lumen. The closable and openable sections of the first and second distal tip sections of the first and second lumens operate thusly: during hemodialysis, negative pressure is applied to the first lumen and blood is drawn from a patient's vessel into the first distal tip and through the first lumen; positive pressure applied to the second lumen when blood enters the proximal end of the second lumen and separates the several lip portions at the second distal tip to re-enter the vessel. Were the reverse of the pressures to be caused by an incorrect hemodialysis connection, blood traveling into the first lumen would open the flap to enter the vessel, while negative pressure on the second lumen would close the several lip sections but open the side ports for blood to enter from the vessel. Between dialysis procedures, locking solution injected under low pressure into the catheter would fill both lumens since the distal tips would be in their closed, undeflected conditions, and when removed, blood from the vessel would enter both distal tips due to negative pressure on both lumens.

It is desired to provide a catheter that will minimize or eliminate the small amounts of locking solution entering a patient's blood stream from an implanted catheter between dialysis treatments.

BRIEF SUMMARY OF THE INVENTION

The present invention is a closable and openable catheter assembly of first and second catheters having respective first and second lumens, first and second distal portions, first and second proximal portions, first and second distal end portions, and first and second proximal end portions; first and second distal openings defined into the first and second distal end portions of the first and second catheters for fluid communication between the first and second lumens with vasculature of a patient when the distal portions of the first and second catheters are implanted in the vasculature; and an actuating assembly in operative association with respect to the first and second catheters, wherein actuation of the actuating assembly actuates at least one of the first and second distal end portions between opened and closed conditions wherein the first and second lumens are in fluid communication with the vasculature of the patient in the opened condition and the first and second lumens are not in fluid communication with the vasculature of the patient.

The present invention also includes an actuator assembly for a closable and openable catheter assembly where the catheter assembly includes a first and second catheter wherein one of the first and second catheters is axially movable with respect to the other to close and open distal openings of the first and second catheters, including a first actuator portion rotatably affixed about one of the first and second catheters, and a second actuator portion nonrotably affixed to the one of the first and second catheters, wherein relative rotation of the first actuator portion with respect to the second actuator portion and between first and second angular stops, permits and prevents respectively, axial movement between first and second axial positions of the second actuator portion with respect to the first actuator portion and also with respect to the other of the first and second catheters, wherein when the second actuator portion is in the first axial position, the distal openings of the first and second catheters are open and when the second actuator is in the second axial position, the distal openings are closed.

Also, the present invention includes a closable and openable catheter assembly, including a first catheter and a second catheter respectively having first and second distal end portions and having respective distal openings to vasculature of a patient when the catheter assembly is implanted within the patient; and each of the first and second distal end portions having respective closure structures to occlude the distal openings of the other when the catheter assembly is actuated to a closed condition, and which do not occlude the distal openings of the other when the catheter is actuated to an opened condition.

In a preferred embodiment, the catheter assembly comprises a dual lumen catheter wherein a first lumen is defined in a separate, generally coaxial inner catheter within an outer catheter and that is movable axially with respect to the second or outer lumen by manipulation remote from the distal end, of a proximal inner catheter end section extending proximally from a hub outside of the patient and separate from the proximal outer catheter end section, all while the assembly remains sealed. The first distal tip of the inner catheter extends at least to some extent distally of the second distal tip of the outer catheter and includes an enlargement, such as a closure cap assembly, sufficiently large in diameter to close off the distal opening of the outer catheter when positioned thereagainst in the closed catheter assembly position. While it is preferred that the enlargement include an aperture therethrough for guide wire placement, a valve traverses the aperture and allows for passage of the guide wire, where upon guide wire removal, the aperture seals closed.

The inner catheter includes at least one side port proximally of the enlargement for fluid communication between the first lumen and the vessel when the inner catheter is in the open position, and the inner catheter side ports are closed by the surrounding outer catheter when the inner catheter is in the closed position. Further, the inner catheter includes a barrier section that blocks and closes all outer catheter side ports preferably from within the outer catheter when the inner catheter is in the closed position, whereby no side ports in either the first lumen or the second lumen are open to the blood vessel when the catheter assembly is closed. Locking solution is successfully kept within the catheter assembly when in the closed position, and fluid flow successfully permitted when the catheter assembly is in the open position.

In a preferred embodiment of distal tip arrangement, the side ports of the outer catheter comprises a pair of elongate slots on opposite sides while the barrier section of the inner catheter comprises a pair of outwardly projecting ribs that are disposed in the respective slots and are movable therealong between forward or open, and rearward or closed, positions with respect thereto when the inner catheter is moved between open and closed positions.

The proximal end section of the inner catheter extends proximally through the hub of the assembly and is movable axially therewithin, and may have secured thereto an extension tube proximally of the hub by a connecting arrangement that is part of the present invention; the outer catheter proximal end may be joined to a respective extension tube within the hub, as is conventional.

Manipulation of the inner catheter between open and closed positions is preferably attained by controlled and limited axial movement of the inner catheter with respect to the assembly and the outer catheter. The proximally disposed actuator assembly for the inner catheter may comprise an adapter sleeve and a swivel sleeve, and the actuator assembly may also serve to connect the inner catheter to a respective extension tube. The swivel sleeve is located adjacent to the proximal hub exit for the inner catheter and provides an inner cylindrical wall surface having defined thereinto a pair of opposed first and second slots spaced axially therealong coextending circumferentially from respective opposed axial slots extending therebetween, defining first and second, or open and closed, positions, with the open position provided by the more distal first slot and the closed position provided by the more proximal second slot. The swivel sleeve is manually rotatable with respect to the assembly about the inner catheter proximally of the hub.

The adapter sleeve of the inner catheter is positioned proximally of the swivel sleeve but has a distal portion extending into the proximal end of the swivel sleeve, which distal portion includes a pair of detents on opposite sides of the distal portion and projecting radially outwardly. The adapter sleeve is movable axially with respect to the swivel sleeve and the hub only when the swivel sleeve has been rotated to an "open" position in which the axial slots are moved into alignment with the detents, which can then move axially along the axial slots and then circumferentially along either the first or second slot portion relative to the swivel sleeve. A pair of stabilizing posts may preferably extend distally from the distal end of the cylindrical body of the adapter sleeve and extend through the swivel sleeve adjacent to its inner surface to stabilize the coaxial orientation of the sleeves when in the closed position, when the adapter sleeve is relatively proximally spaced from the swivel sleeve. Visual indicators preferably are provided on both the adapter sleeve and the swivel sleeve, for the practitioner to determine the location of the slot followers with respect to the first and second slot portions to indicate the open or closed positions.

A method of the present invention comprises the steps of providing a catheter having an outer catheter and an inner catheter to which a hub is secured along the proximal portions thereof, the inner and outer catheter having respective distal portions extending to respective distal tip portions, and the inner catheter being movable axially within and along the outer catheter and the hub by an actuator assembly of the inner catheter to move a distal tip of the inner catheter relative to the distal tip portion of the outer catheter to open and close both catheters; and actuating the actuator assembly to move the inner catheter axially with respect to the outer catheter and the hub to move the inner catheter distal tip portion between open and closed positions relative to the outer catheter distal tip portion, to open and close the distal openings of both the inner and outer catheter lumens.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 3 and 4 are longitudinal cross-sectional views of the catheter assembly of FIGS. 1 and 2, with the catheter assembly in the closed and opened positions, respectively;

FIGS. 5 and 6 are enlarged cross-sectional views of the distal end portion of the assembly of FIGS. 3 and 4 in the closed and opened positions, respectively, taken along lines 5-5 and 6-6 thereof, respectively;

FIGS. 7 and 8 are elevation and top views of the outer catheter's distal end portion, respectively, with an outer sleeve exploded therefrom in FIG. 7;

FIGS. 9 to 11 are top, elevation and cross-sectional views of the inner catheter's distal end portion, respectively, with the closure cap exploded therefrom in FIG. 9 and the cross-sectional view taken along lines 11-11 of FIG. 9;

FIGS. 15 and 16 are isometric views of the adapter sleeve and the swivel sleeve, respectively that comprise the actuator assembly for the inner catheter;

FIG. 17 is a diagrammatic view of the interior surface of the swivel sleeve of FIG. 16;

FIGS. 18 and 19 are enlargements of the hub of the assembly of FIGS. 3 and 4, in cross-section, in the closed and opened positions, taken along lines 18-18 and 19-19 of FIGS. 3 and 4, respectively.

DETAILED DESCRIPTION OF THE INVENTION

Figure 1:
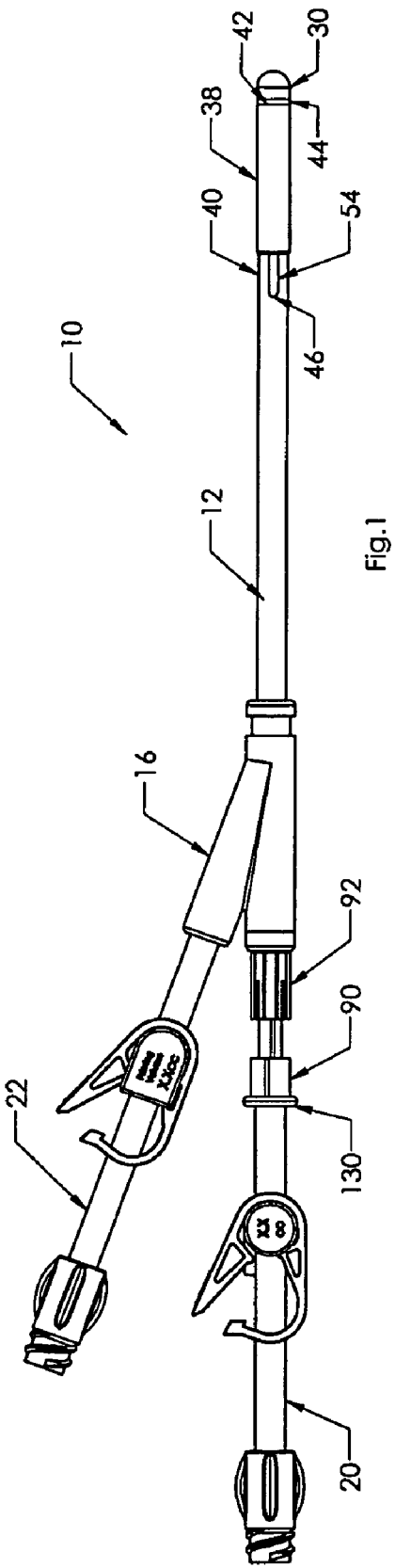
FIGS. 1 and 2 are elevations view of the catheter assembly of the present invention in the closed and open positions, respectively.

In the drawings, like numerals indicate like elements throughout. Certain terminology is used herein for convenience only and is not to be taken as a limitation on the present invention. The term "distal" is meant to describe the portion of a catheter according to the present invention that is inserted into a patient, and the term "proximal" is meant to describe the portion of a catheter according to the present invention that remains exterior of the patient. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

FIGS. 1 to 4 illustrate a catheter assembly 10 of the present invention in a closed condition and an open condition, respectively. The length of the catheter assembly has been shortened from its desired actual length. Catheter assembly 10 includes an outer catheter 12, an inner catheter 14 (FIGS. 3 and 4), a hub 16, a first extension tube assembly 18 affixed to the proximal end 20 of the catheter assembly 10 in fluid communication with the inner catheter 14, and a second extension tube assembly 22 affixed to the hub 16 to be in fluid communication with outer catheter 12 within hub 16. The first and second extension tube assemblies are shown to include clamps therealong and luer fittings or connectors at proximal ends thereof, as is conventional. Preferably, the hub is insert-molded about the proximal end portion of the outer catheter. Through the use of mandrels and/or core pins (not shown), the hub 16 is molded to include an angled passageway 24 (FIGS. 3, 4 and 20) providing fluid communication between the lumens of the outer catheter and its extension tube assembly 22; the hub also is molded to include a linear passageway 26 therethrough into which a proximal end portion 128 (see FIG. 19) of the inner catheter 14 will extend as it exits from the proximal end 28 of the outer catheter to be joined to a steel cannula 29 such as by being expanded to extend over a distal end portion of the steel cannula forming a tight, sealed grip thereto, defining an inner catheter/steel cannula subassembly. Steel cannula 29 will continue through linear passageway 26 and protrude from hub 16; the inner catheter/steel cannula subassembly 14,29 is axially movable with respect to the outer catheter 12 and the hub 16.

In accordance with the present invention and referring primarily to FIGS. 1 to 4, a closure cap assembly 30 containing therewithin a valve is secured to the distal tip section 32 of inner catheter 14 and closes off the distal end opening 34 (see FIG. 12) of the lumen of the inner catheter. Closure cap assembly 30 is also sufficiently large in diameter to close off the distal tip opening 36 (FIGS. 7 and 8) of the lumen of outer catheter 12 when the catheter assembly is in the closed position. Preferably, a containment sleeve 38 is affixed about, and is conterminous with, a distal end portion 40 of outer catheter 12 and having a distal sleeve end 42 that abuts a proximal surface 44 of closure cap assembly 30 when the catheter assembly is in the closed condition.

Seen in FIGS. 1 to 4, outer catheter 12 of the present invention preferably includes a pair of elongate side slots 46 along the distal end portion 40, permitting fluid communication of the lumen with the vasculature of the patient (when the catheter assembly is in the open condition). Side slots 46 are shown to extend to the distal tip of outer catheter 12, at distal tip opening 36 (see FIG. 8); this is not required for operation of the invention, but is practical from a manufacturing and assembly standpoint. Inner catheter 14 also includes side slots 48 along its distal end portion 50, extending proximally from proximal surface 44 of closure cap assembly 30, establishing fluid communication with the vasculature of the patient when the catheter assembly is in the open condition.

Portions 52 of the inner catheter side wall appear in FIGS. 2 and 4 to 6 between the side slots 48, joining the closure cap assembly 30 to the main portion of the inner catheter 14. Inner catheter 14 further includes a pair of elongate ribs 54 along opposite sides of distal end portion 50, best seen in FIGS. 9 to 12, extending proximally from side wall portions 52; elongate ribs 54 are associated with elongate slots 46 of outer catheter 12 and are disposed therein and therealong upon assembly of the catheter assembly. Elongate ribs 54 are movable axially within elongate slots 46 during axial movement of the inner catheter with respect to the outer catheter 12 during actuation of the assembly between its opened and closed conditions, to open the outer catheter for fluid transmission therethrough. Distal tip section 32 of inner catheter 14 is defined distally of side slots 48 and side wall portions 52, and becomes part of the closure cap assembly 30. It is preferable for the distal end portion 50 of inner catheter 14 to undergo an insert molding manufacturing procedure for defining the elongate ribs 54 and the distal tip section 32, which preferably includes formation of a surrounding sleeve 56 that serves to block communication between the inner catheter 14 and the outer catheter 12, which is best shown in FIG. 12.

Figure 2:
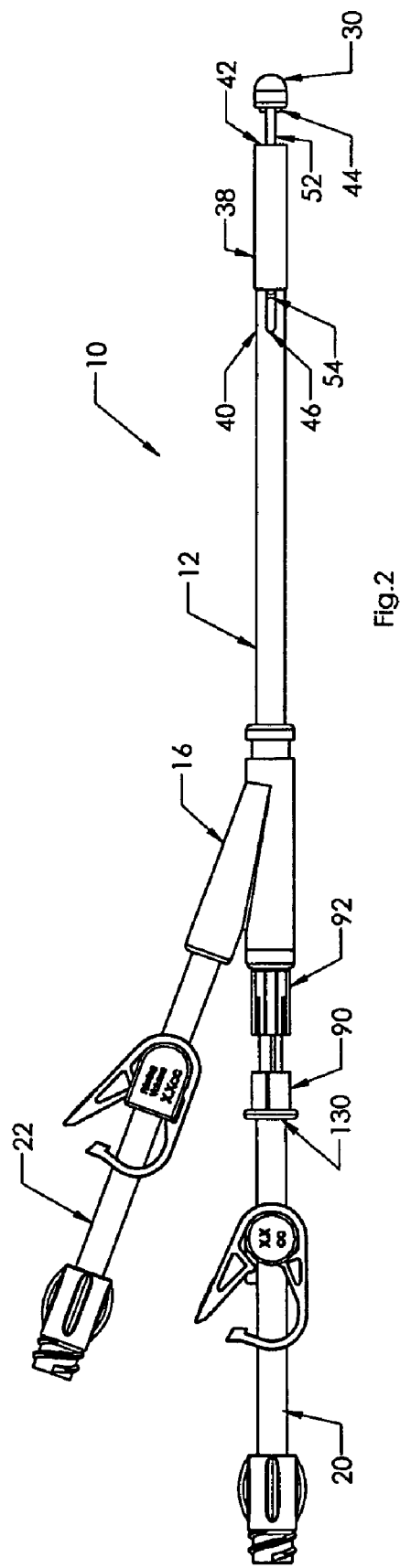

Now referring to FIGS. 7 and 8, distal end portion 40 of outer catheter 12 is seen to have a pair of opposed elongate slots 46 extending to the distal end thereof, in communication with the lumen of outer catheter 12 for fluid transmission with the vasculature of the patient when the catheter assembly of the present invention is in the opened condition. Containment sleeve 38 is affixed to the distal end portion 40 after assembly of the inner catheter within the outer catheter, and may be prepositioned along the outer assembly proximally of the distal end portion during assembly and then slid into position, acting to seal the outer catheter by covering most of the length of the elongate slots 46, and also the elongate ribs 54 of the inner catheter, except for preselected proximal slot portions as seen in FIGS. 1 and 2 which are open to the vasculature when the elongate ribs 54 therein are in their distalmost positions when the catheter assembly is in the opened condition.

Figure 12:
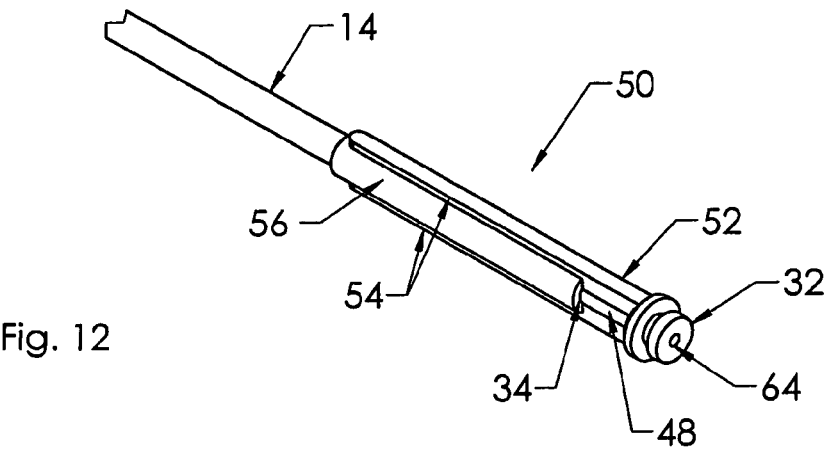
FIG. 12 is an enlarged isometric view of the inner catheter's distal end portion.

In FIGS. 9 to 12, the distal end portion 50 of inner catheter 14 is shown, having sleeve 56 molded thereonto and including elongate ribs 54 and distal end section 32. Cap member 58 is shown in FIG. 9 positioned to be affixed onto distal end section 32 of inner catheter 14. Sleeve 56 is best shown in FIGS. 11 and 12.

Figure 13:
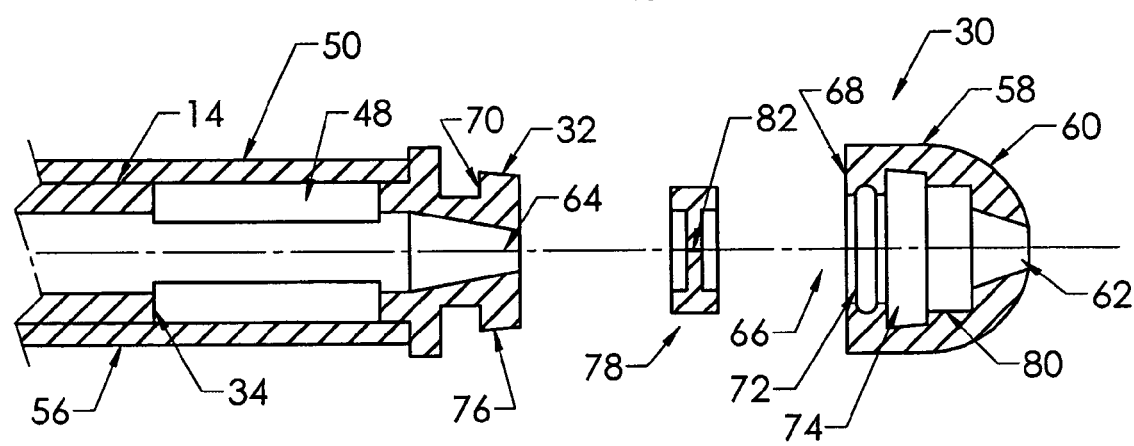
FIGS. 13 and 14 are enlarged cross-sectional views of the inner catheter distal end with the closure cap components, in the exploded and assembled relationships, respectively.
Figure 14:
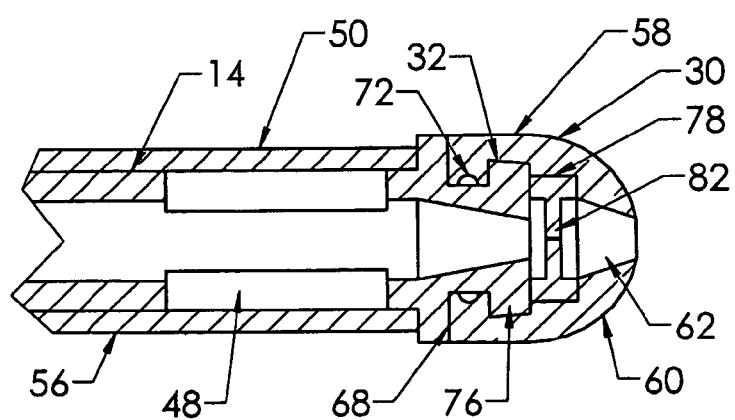

The structure of closure cap assembly 30 will now be described in detail with respect to FIGS. 13 and 14. Cap member 58 includes a domed distal face 60 and includes a small diameter hole therethrough and centered with respect to domed distal face 60; hole 62 permits insertion and implantation of the catheter assembly into the vasculature of a patient through the use of a small diameter guide wire (not shown), as is conventional, facilitating the various curves and bends in the vasculature in order to precisely position the distal tip of the catheter assembly in position. Hole 62 is aligned with a corresponding hole 64 into distal end section 32 of inner catheter 14, which in turn is centered with respect to the lumen of the inner catheter when cap member 60 is assembled to distal end section 32. Cap member 60 further includes a shaped proximal cavity 66 having a capture flange 68 complementary to a capture recess 70 of distal end section 32 to physically secure the cap member to the distal end section; an annular groove 72 is formed into capture flange 66 for placement of a bead of adhesive to bond cap member 58 to distal end section 32. Cap member 58 further preferably includes a capture recess 74 distally of capture flange 68, into which becomes seated a distalmost flange 76 of distal end section 32.

A valve 78 is inserted into cap member 58, being seated in valve seat 80 in the distal portion of proximal cavity 66. Valve 78 is shown to include a slit 82 partially transversely thereacross, which slit is normally closed but which is openable to permit passage therethrough of a guide wire. Tapering or funneling surfaces are defined through distal end section 32 and the distal end of cap member 58 to act as lead-ins for facilitating the insertion through the small diameter holes 62,64, of a guide wire in the event that the catheter assembly after initial implantation were to be removed and replaced. Valve 78 remains closed after the catheter assembly has been implanted in the vasculature and the guide wire removed, even when the catheter assembly is in the opened condition since hole 62 is not used for fluid transmission.

Turning now to FIGS. 15 to 17, an adapter sleeve 90 and a swivel sleeve 92 will now be described, that comprise the actuator assembly for axial movement of the inner catheter 14. Adapter sleeve 90 has a proximal end projection 94 over which will be fitted the distal end of the extension tube assembly 20, as seen in FIGS. 1 to 4; thus, adapter sleeve 90 serves as the connector of the extension tube assembly 20 to the inner catheter 14. An annular collar 96 is located proximal to cylindrical body section 98, and a smaller diameter distal section 100 extends distally from body section 98 to end faces 102. A pair of detent projections or detents 104 are positioned on opposite sides of distal section 100 adjacent end faces 102. A pair of stabilizing struts 106 extend distally forwardly from distal section 100.

Swivel sleeve 92 is cylindrical, having a proximal end 108 and a distal end 110. An array of grooves 112 preferably is formed on the exterior side surface thereof to facilitate manual gripping of the swivel sleeve during rotation thereof by the practitioner, during opening and closing the catheter assembly. Referring particularly to the diagram of FIG. 17, into and along the interior surface 114 of swivel sleeve 92 is a slot arrangement 116 with which the pair of detents 104 of the adapter sleeve 90 cooperate to move the inner catheter/steel cannula subassembly 14,29 to defined fully opened and fully closed positions of the inner catheter 14. Slot arrangement 116 comprises a pair of opposed axially extending slot portions 118, circumferentially extending distal slot portions 120 and circumferentially extending proximal slot portions 122 communicating with axially extending slot portions 118. At the proximal ends of the axially extending slots are seen short slot portions 126 extending to the proximal end 108 that permit positioning of the detents 104 of adapter sleeve 90 into the slot arrangement 116 during assembly of the adapter sleeve and the swivel sleeve to the steel cannula 29 as it projects proximally from the hub 16 (see FIGS. 3, 4, 18 and 19).

With respect to FIGS. 18 to 21, the structure and operation of the actuation assembly 130 of the catheter assembly of the present invention will now be described. Actuator assembly 130 is affixed to the inner catheter proximal portion 128 in such a manner that adapter sleeve 90 and inner catheter 14 together are able to move axially with respect to swivel sleeve 92; detents 104 are able to be moved axially along axial slot portions 118 between the slot portions 120,122. Swivel sleeve 92 is rotatably movable with respect to the adapter sleeve 90 and the inner catheter 14, with detents 104 able to follow circumferential slot portions 122 at the proximal end of swivel sleeve 92 in an angular direction, or to follow circumferential slot portions 120 at the distal end 110 of the swivel sleeve in an angular direction opposite from that related to slot portions 122, corresponding to the closed condition and the opened condition, respectively, of the catheter assembly of the present invention.

Actuator assembly 130 is affixed to the hub 16 in the following manner. Two additional components are utilized, preferably along with an o-ring, that are disposed primarily within the hub proximal end portion 132 associated with the inner catheter 14 and steel cannula 29 to which it is joined, in order to permit rotation of swivel sleeve 92 as well as sealing with respect to the inner catheter but which permits axial movement of the inner catheter 14 with respect to the hub. Linear passageway 28 of hub 16 receives thereinto a generally tubular outer sleeve component 134 that is bonded therewithin; outer sleeve 134 includes an external antirotation rib 136 preventing its rotation with respect to hub 16 and also serving as an antirotation strain relief in cooperation with a corresponding slot of the hub thereover (FIGS. 18 to 21). A generally tubular inner sleeve component 138 is disposed within outer sleeve component 134 and around steel cannula 29, and an o-ring seal 140 is disposed in the distal end 142 of outer sleeve 134 and is abutted by the distal end 144 of the inner sleeve upon assembly; o-ring 140 sealingly engages the outer surface of steel cannula 29 in a manner which permits the inner catheter/steel cannula subassembly 14,29 to move axially between opened and closed positions (see FIG. 21) and also defines a seal between the interior passageways of the hub and the proximal exit for steel cannula 29. Preferably, inner sleeve 138 is bonded to outer sleeve 134.

Figure 20:
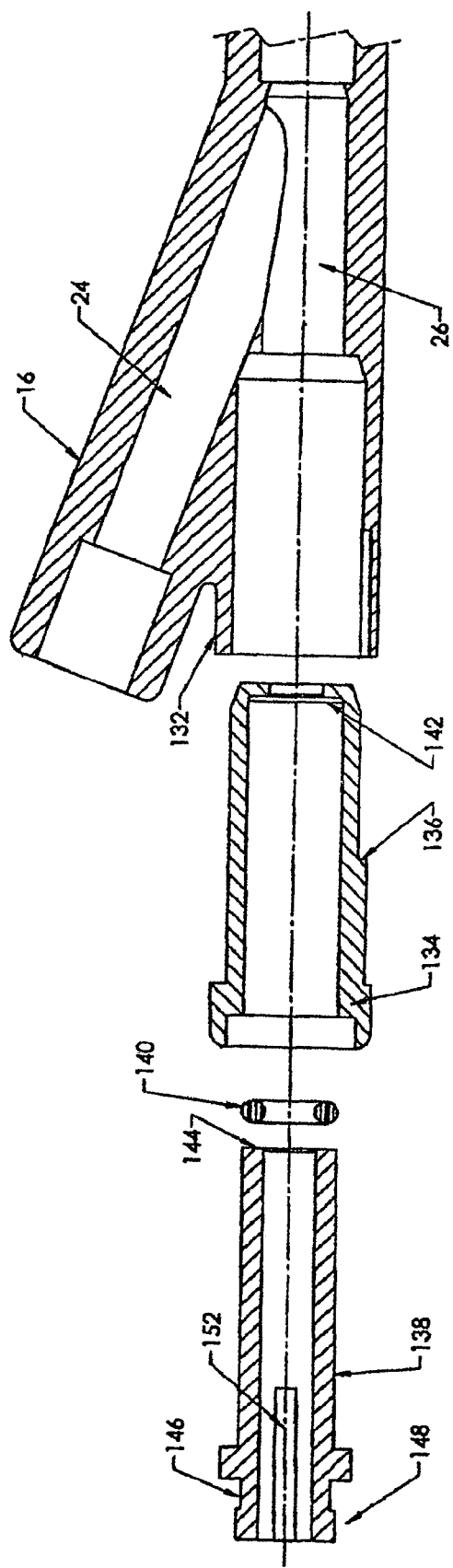
FIGS. 20 and 21 are exploded cross-sectional views of the proximal end of the hub showing the components that will be secured to the catheter assembly at the proximal end of the hub and with respect to the inner catheter, respectively, that will enable remote movement of the distal tip of the inner catheter, with FIG. 21 showing the adapter and swivel sleeves of FIGS. 15 and 16.
Figure 21:
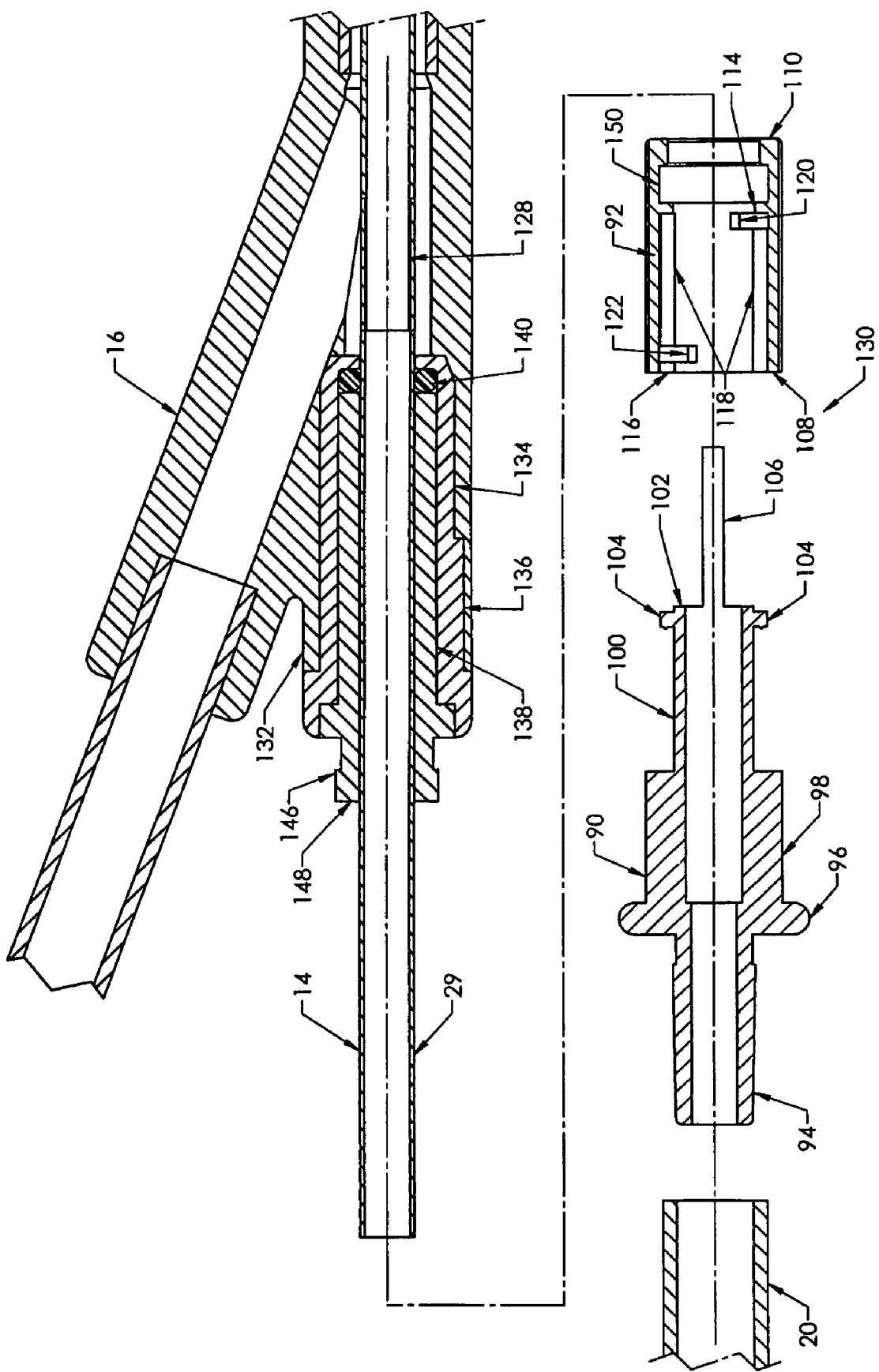

Inner sleeve 138 includes a flange/recess capture section 146 at its proximal end 148, complementary to a corresponding flange/recess capture section 150 at the distal end 110 of swivel sleeve 92. The flange/recess capture sections permit relative rotational movement of the swivel sleeve with respect to the hub 16 and, actually, the entire catheter assembly. Also, as seen in FIG. 20, inner sleeve 138 includes a pair of strut-receiving slots 152 extending distally from the proximal end 148, whereinto extend the stabilizing struts 106 of adapter sleeve 90 of the actuator assembly as the struts extend distally beyond the distal end 110 of the swivel sleeve when the catheter assembly 10 is in its opened condition and the inner catheter has been translated to its distalmost position.

Visual indicators are preferably provided with the catheter assembly 10 of the present invention to provide a clear indication to the practitioner whether the inner catheter is in its closed condition or its opened condition, since the distal portion of the catheter assembly is within the vasculature of the patient while the proximal portion including the hub 16 is external to the patient. A pair of axially extending marker stripes 160 are provided on the external surface of the swivel sleeve 92 at preselected angular locations on opposite sides of the sleeve. The adapter sleeve 90 is provided with two pairs of axially extending marker stripes 162,164: one pair of marker stripes 162 is provided on the external surface of the section 98 and are associated with the opened condition of the catheter assembly, and become aligned with and adjacent to respective ones of the marker stripes 160 of the swivel sleeve when the adapter sleeve is in its distalmost position adjacent the swivel sleeve and fully rotated so that the detents are located at the termini of the distal slot portions 120 in the swivel sleeve; another pair of marker stripes 164 is provided on the external surface of the distal section 100 of the adapter sleeve, angularly offset from marker stripes 162 so that stripes 164 become revealed when the adapter sleeve 90 has been axially translated proximally from swivel sleeve 92, and become aligned with marker stripes 160 of the swivel sleeve 92 when the swivel sleeve 92 has been rotated so that detents 104 are located at the termini of the proximal slot portions 122 in the swivel sleeve.

The various components of the present invention may be made from the following materials: inner and outer catheters 14,12 may be made for example of silicone, or may be of polyurethane; distal sleeve 56 defining the structure at the distal end of inner catheter 14 is preferably molded of material identical to that of the inner catheter; containment sleeve 38 for outer catheter 12 may be of material identical to that of the outer catheter; cap component 58 may be made of polyurethane; valve 78 may be made of silicone; hub 16 may be made of polyurethane; adapter sleeve 90, swivel sleeve 92, outer sleeve 134 and inner sleeve 138 may be made of polyvinyl chloride; o-ring 140 may be made of silicone; and the extension tubes 20,22 may be made of polyurethane as is conventional.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A closable and openable catheter assembly, comprising:
   first and second catheters having respective first and second lumens, first and second distal portions, first and second proximal portions, first and second distal end portions, and first and second proximal end portions, the first and second catheters co-axial with one of the catheters of the first and second catheters within the lumen of the other catheter of the first and second catheters;
   at least one distal opening defined by the first distal end portion of the first catheter for fluid communication between the first lumen and an exterior of the first catheter and at least one distal opening defined by the second distal end portion of the second catheter for fluid communication between the second lumen and an exterior of the second catheter; and
   an actuating assembly in operative association with respect to the first and second catheters, wherein actuation of the actuating assembly actuates at least one of the first and second distal end portions between opened and closed conditions wherein in the opened condition fluid is free to pass into or out of the first and second lumens through the respective distal openings and in the closed condition fluid is substantially prevented from passing into or out of the first and second lumens through the respective distal openings, and wherein, in either the opened or closed condition, the first and second lumens are not in direct fluid communication with one another through the distal openings.

2. The catheter assembly of claim 1, wherein the catheter assembly includes visual indicators related to the closed and opened conditions of the catheter assembly proximate to at least one of the first and second proximal portions.

3. The catheter assembly of claim 1, wherein the actuating assembly effectuates movement of one of the first and second distal end portions relative to the other thereof.

4. The catheter assembly of claim 3, wherein the actuating assembly axially translates the one of the first and second catheters.

5. The catheter assembly of claim 4, wherein the first catheter is coaxially disposed within and along the second catheter, and the actuating assembly axially translates the first catheter with respect to the second catheter.

6. The catheter assembly of claim 5, wherein the first distal end portion closes the at least one distal opening of the second catheter, and the second distal end portion closes the at least one distal opening of the first catheter, when the catheter assembly is in its closed condition.

7. The catheter assembly of claim 6, wherein the at least one distal opening of the second catheter extends radially through a side of the second distal end portion.

8. The catheter assembly of claim 6, wherein the at least one distal opening of the second catheter includes a pair of openings on opposed sides of the second catheter distal end portion.

9. The catheter assembly of claim 8, wherein each opening of the pair of openings is an axially extending elongate slot.

10. The catheter assembly of claim 6, wherein the at least one distal opening of the first catheter extends radially through a side of the first distal end portion.

11. The catheter assembly of claim 6, wherein the at least one distal opening of the first catheter includes a pair of openings on opposed sides of the first distal end portion.

12. The catheter assembly of claim 11, wherein the pair of openings is occluded by the second distal end portion when the catheter assembly is in the closed condition.

13. The catheter assembly of claim 12, wherein the first catheter includes a closure cap assembly disposed on a distal tip of the first catheter, and the closure cap assembly occludes a distal tip opening of the first lumen.

14. The catheter assembly of claim 13, wherein the closure cap assembly includes a small diameter distal tip opening and further includes a valve therewithin to occlude the small diameter distal tip opening when a medical device is not extending through the small diameter distal tip opening.

15. The catheter assembly of claim 1, wherein the actuating assembly includes a first actuator portion rotatably affixed about the first catheter or an extension thereof, and a second actuator portion nonrotatably affixed to the first catheter or the extension thereof, wherein relative rotation of the first actuator portion with respect to the second actuator portion and between first and second angular stops, permits and prevents respectively, axial movement between first and second axial positions of the second actuator portion with respect to the first actuator portion and also with respect to the second catheter, wherein when the second actuator portion is in the first axial position, the respective distal openings of the first and second catheters are open and when the second actuator is in the second axial position, the respective distal openings of the first and second catheters are closed.

16. A closable and openable catheter assembly, comprising:
    first and second catheters having respective first and second lumens, first and second distal portions, first and second proximal portions, first and second distal end portions, and first and second proximal end portions;
    at least one distal opening defined into the first distal end portion of the first catheter and at least one distal opening defined into the second distal end portion of the second catheter for fluid communication between the first and second lumens with vasculature of a patient when the distal portions of the first and second catheters are implanted in the vasculature; the at least one opening of the second distal end portion includes a pair of side openings which are axially extending elongate slots on opposed sides of the second catheter distal end portion, and
    an actuating assembly in operative association with respect to the first and second catheters, wherein actuation of the actuating assembly actuates at least one of the first and second distal end portions between opened and closed conditions wherein the first and second lumens are in fluid communication with the vasculature of the patient in the opened condition and the first and second lumens are not in fluid communication with the vasculature of the patient in the closed condition;
    wherein the actuating assembly effectuates movement of one of the first and second distal end portions relative to the other thereof with the first catheter coaxially disposed within and along the second catheter, and the actuating assembly axially translates the first catheter with respect to the second catheter such that the first distal end portion closes the at least one distal opening of the second distal end portion of the second catheter, and the second distal end portion closes the at least one distal opening of the first distal end portion of the first catheter, when the catheter assembly is in its closed condition, and wherein the first distal end portion includes a pair of elongated ribs projecting outwardly from exterior side wall surfaces of the first catheter associated with and axially movable within and along the elongate slots of the second distal end portion to partially occlude at least portions of the elongate slots when the catheter assembly is in the opened condition, and to occlude remaining portions of the elongate slots when the catheter assembly is in the closed condition.

17. The catheter assembly of claim 16, wherein the second distal end portion includes a containment sleeve therearound closing the portions of the elongate slots along and within which extend the elongated ribs of the first distal end portion when the catheter assembly is in the opened condition but reveals the remaining portions of the elongate slots such that the remaining portions are closable only by the elongated ribs.

18. A closable and openable catheter assembly, comprising:
    first and second catheters having respective first and second lumens, first and second distal portions, first and second proximal portions, first and second distal end portions, and first and second proximal end portions;
    at least one distal opening defined into the first distal end portion of the first catheter and at least one distal opening defined into the second distal end portion of the second catheter for fluid communication between the first and second lumens with vasculature of a patient when the distal portions of the first and second catheters are implanted in the vasculature; and
    an actuating assembly in operative association with respect to the first and second catheters, wherein actuation of the actuating assembly actuates at least one of the first and second distal end portions between opened and closed conditions wherein the first and second lumens are in fluid communication with the vasculature of the patient in the opened condition and the first and second lumens are not in fluid communication with the vasculature of the patient and are not in direct fluid communication with one another through the respective distal openings in the closed condition;
    wherein the actuating assembly effectuates movement of one of the first and second distal end portions relative to the other thereof by axially translating the one of the first and second catheters and wherein the actuating assembly is operatively affixed to the one of the first and second catheters and includes a first portion that is rotatable with respect to the one of the catheters and a second portion that is operably affixed to the one of the catheters and is axially movable with respect to the first portion and the other of the first and second catheters, effecting relative axial movement of the one of the first and second catheters with respect to the other of the first and second catheters thereof.

19. The catheter assembly of claim 18, wherein the catheter assembly includes visual indicators related to the closed and opened conditions of the catheter assembly.

20. The catheter assembly of claim 19, wherein the visual indicators include at least one stripe along an exterior surface of the first portion of the actuator assembly and at least one corresponding stripe along an exterior surface of the second portion, all such that the stripes become axially aligned to indicate a selected one of the closed and opened conditions.

21. The catheter assembly of claim 20, wherein the visual indicators include at least one stripe on the second portion associated with a closed condition of the catheter assembly, and at least a second stripe on the second portion associated with an opened condition of the catheter assembly.

22. The catheter assembly of claim 21, wherein the second portion of the actuating assembly includes a body section and a distal section distal of the body section, wherein the distal section has a diameter such that it is receivable into the first portion of the actuating assembly, and wherein the at least one stripe on the second portion associated with the closed condition, is disposed on the exterior surface of the distal section of the second portion and becomes hidden within the first portion when the catheter assembly is in the opened condition, and the at least one stripe associated with the opened condition is disposed on an exterior surface of the body section and is angularly offset from the at least one stripe associated with the closed condition but which becomes aligned with the at least one stripe of the first portion when the first portion is rotated to a stop position indicating that the catheter assembly is in its opened condition.

23. The catheter assembly of claim 18, wherein a hub of the catheter assembly is affixed to the other of the first and second catheters, and the one of the first and second catheters is movable with respect to the hub during actuation between the closed and opened conditions by the actuating assembly.

24. The catheter assembly of claim 23, wherein the catheter assembly includes a seal within the hub establishing a sealed relationship between interior passageways of the hub and a hub exit through which extends the one of the first and second catheters.

25. The catheter assembly of claim 23, wherein the first portion of the actuating assembly surrounds the one of the first and second catheters along its respective proximal end portion and is rotatably affixed to the hub.

26. The catheter assembly of claim 25, wherein the first portion of the actuating assembly includes defined along and into an interior surface thereof a slot arrangement having axial and circumferential slot portions, and the second portion of the actuating assembly includes, defined along and outwardly from an exterior surface thereof adjacent a distal end thereof, a detent arrangement cooperable with the slot arrangement to permit relative axial movement of the first and second portions and to define the closed and opened conditions of the catheter assembly and retain the closed and opened conditions after actuation.

27. The catheter assembly of claim 26, wherein the second portion of the actuating assembly is located proximally of the first portion thereof, and includes a stabilizing section for maintaining an axially aligned and coaxial orientation of the one of the first and second catheters with respect to the first portion.

28. The catheter assembly of claim 27, wherein the stabilizing section comprises a pair of struts projecting distally from the distal end of the second portion and into the first portion of the actuating assembly to be adjacent the interior surface of the first portion.

29. The catheter assembly of claim 28, wherein the hub includes a pair of opposing slots associated with the struts of the second portion of the actuator assembly, to receive thereinto and therealong distally projecting portions of the struts when the second portion has been axially moved to a distal-most location and the struts extend distally beyond the first portion of the actuator assembly.

* * * * *